United States Patent [19]

House

[11] 4,418,225

[45] Nov. 29, 1983

[54] RESOLUTION OF D,1-MENTHOL

[75] Inventor: David W. House, Arlington Heights, Ill.

[73] Assignee: UOP Inc., Des Plaines, Ill.

[21] Appl. No.: 338,443

[22] Filed: Jan. 8, 1982

[51] Int. Cl.³ .............................................. C07C 35/12
[52] U.S. Cl. .................................................. 568/829
[58] Field of Search ........................................ 568/829

[56] References Cited

U.S. PATENT DOCUMENTS

| | | | |
|---|---|---|---|
| 2,760,993 | 8/1956 | Chang | 568/829 |
| 3,109,018 | 10/1963 | Hanover | 260/475 |
| 3,305,591 | 2/1967 | Epstein et al. | 260/631 |
| 3,607,651 | 9/1971 | Moroe et al. | 195/30 |
| 3,620,918 | 11/1971 | Moroe et al. | 195/2 |
| 3,943,181 | 3/1976 | Fleischer et al. | 260/631 |

FOREIGN PATENT DOCUMENTS

| | | | |
|---|---|---|---|
| 40-2545 | 10/1965 | Japan | 568/829 |
| 49-36226 | 9/1974 | Japan | 568/829 |
| 55-111427 | 8/1980 | Japan | 568/829 |

OTHER PUBLICATIONS

Chem. Eng., May 22, 1978, 62-3.
Harada & Hayakawa Bull., Chem. Soc. Japan, 37, 191, (1964).
Halpern & Westley, Chem. Comm., 421, (1965).
Advances in Chromatography, vol. 16, pp. 177-183, (1978).

Primary Examiner—Werren B. Lone
Attorney, Agent, or Firm—James R. Hoatson, Jr.; Eugene I. Snyder; William H. Page, II

[57] ABSTRACT

1-Menthol can be readily obtained from racemic menthol by conversion of the latter to the diastereomeric esters of an optically active amino acid and chromatographing the diastereomers. The separation of the diastereomeric esters is relatively insensitive to the support or to the solvent used as eluant, and satisfactory separation occurs under a broad variety of conditions. 1-Menthol can be obtained by base catalyzed hydrolysis of the purified diastereomer with high optical purity.

14 Claims, No Drawings

RESOLUTION OF D,1-MENTHOL

This application relates to a method of preparing optically active menthol from its racemic mixture. In particular, the invention disclosed herein relates to the resolution of d,l-menthol into its enantiomers. More particularly, the method of this invention relates to obtaining l-menthol in high yield from its racemic mixture.

Menthol is widely used in a broad spectrum of products, for example, in liquers, confectionaries, perfume, cigarettes, cough drops, nasal drops and sprays, and is also used, for example, as a topical antipruritic, a mild local anesthetic, an antiseptic, a carminative, and gastric sedative. In virtually all cases, the levorotatory enantiomer, or l-menthol, is preferred. However, because of its increased demand, it has become impossible to meet the commercial requirements for l-menthol from peppermint oil, its natural source of supply, and there has been a concomitant increase in the need for a synthetic source of l-menthol.

A shortcoming of present synthetic methods is that the product is racemic, i.e., d,l-menthol. The challenge is either to prepare l-menthol directly by a synthetic scheme utilizing a chiral environment, or to efficiently obtain l-menthol from its racemate. Although substantial progress has been made in syntheses in a chiral environment, for example, use of chiral reagents, nonetheless the more usual way of preparing optically active material from inactive precursors is by direct or indirect separation of one or both of the components from a racemic mixture, i.e., the classical method of optical resolution.

One method of optical resolution infrequently used is the induction of a phase change of a racemic mixture in a chiral environment, thereby causing a preferential phase change in but one of the enantiomers. This principal is employed in U.S. Pat. No. 3,943,181 where a supersaturated solution of an ester of racemic menthol with benzoic acid, a substituted benzoic acid, or cyclohexanecarboxylic acid is seeded with crystals of the l-menthyl ester, thereby causing preferential precipitation of the l-menthyl ester. Although elegant in its simplicity, the method demands stringent temperature control to within about 0.01° C. (Chem. Eng., May 22, 1979, pp. 62–3).

Other methods of optical resolution utilize the different physical properties of diastereomers to purify at least one diastereomer by some conventional separation method. The desired enantiomer, in this case l-menthol, is then obtained from the purified diastereomer by an appropriate chemical conversion. Fractional or selected crystallization commonly is employed as the method of separating diastereomers. For example, in U.S. Pat. No. 3,109,018 the hydrogen phthalate ester of racemic menthol is reacted with 0.5 mole of optically active 1-(1-naphthyl)ethylamine and 1 mole of ammonia in an organic solvent to afford diastereomeric salts whose solubility in water differs drastically, thereby permitting the isolation and purification of one of the diastereomers. Subsequent acid treatment of the purified diastereomer affords the hydrogen phthalate ester which is subsequently hydrolyzed to afford l-menthol. A similar resolution of menthol could be based on the work of Harada and Hayakawa, *Bull. Chem. Soc. Japan,* 37, 191 (1964), who fractionated the diastereomeric hydrochloride salts of the menthyl ester of amino acids by seeding a supersaturated solution with one diastereomer, or on the work of Halpern and Westley, *Chem. Comm.,* 421 (1965), who observed that the diastereomeric para-toluenesulfonate salts of menthyl esters of amino acids could be readily fractionally crystallized. An interesting resolution of menthol is described in U.S. Pat. No. 3,305,591 where a solution of the racemate, preferably containing an acid, is contacted under interesterification conditions with an insoluble, cross-linked, optically active polymer containing ester groups and acting as the solid phase under chromatographic conditions. Presumably the process involves reversable diastereomer formation under dynamic equilibrium conditions, thereby effecting separation as the enantiomers are eluted from the column. Although this process is one where resolution via chromatographic separation of a racemate is achieved by a chiral stationary phase, the more usual process is chromatographic separation of diastereomers by an achiral stationary phase, as described, for example, in "Advances in Chromatography," Vol. 16, pp. 177–83 (1978). Resolution of menthol also has been achieved by preferential enzymatic hydrolysis as described in U.S. Pat. Nos. 3,607,651 and 3,620,918.

For a chromatographic separation of diastereomers to be commercially successful as a method of resolving menthol, stringent requirements are placed on the diastereomers. One requirement is that optically active menthol must be regenerable in high chemical and optical yield. Another requirement is that the diastereomers be readily separable on a wide variety of stationary phases and using a diversity of eluants, so that the method itself is relatively insensitive to changes in supply and quality of materials, and is relatively undemanding in process control. A basic observation which acts as a foundation for this invention is that diastereomeric esters of certain optically active amino acids and racemic menthol are readily separable under a broad diversity of chromatographic conditions. Since the optically active enantiomers of menthol are readily regenerable from the separate diastereomers by various means in high chemical and stereochemical yield and purity, the aforementioned observation provides the basis for a particularly successful method of resolving menthol. Additionally, the optically active amino acid also can be recovered in high yield to be reused in other cycles of diastereomer preparation, separation, and enantiomeric menthol regeneration.

SUMMARY OF THE INVENTION

An object of this invention is to obtain l-menthol from its racemate. An embodiment is a process comprising the chromatographic separation of an ester of racemic menthol with an optically active amino acid, treating a purified diastereomer to liberate l-menthol, and recovering the l-menthol regenerated thereby. In a more specific embodiment, the amino acids are naturally occurring amino acids. In a still more specific embodiment the naturally occurring amino acids have the L-configuration. In yet another embodiment the amino acid is l-phenylglycine.

DESCRIPTION OF THE INVENTION

The invention described herein is a method of preparing optically active menthol comprising contacting a solution of the diastereomeric esters from racemic menthol and an optically active amino acid with a chromatographic support, eluting the support with a solvent under chromatographic conditions, collecting at least one effluent fraction containing a purified diastereomer, treating the purified diasteromer to liberate optically active menthol, and recovering the menthol. This invention is made possible by the observation that the diastereomeric esters of menthol and amino acids are easily separated on a variety of chromatographic supports with a diversity of solvents as eluants.

Diastereomers are compounds with at least two chiral centers, at least one of which is different and at least one of which is the same. In the case where the diastereomers contain two chiral centers, there are two sets of diastereomers, each set being composed of two enantiomers. The members of each diastereomeric set differ in that one chiral center is the same and the other center is different. For example, where A represents an amino acid, M represents menthol, and the notations d and l represent rotations of polarized light, the diastereomeric sets of the esters of menthol with amino acids are, (1) l-M-d-A
(2) d-M-l-A
(3) l-M-l-A
(4) d-M-d-A where (1) and (2) are enantiomers, as are (3) and (4), but both (1) and (2) are diastereomers of both (3) and (4). In particular, (2) and (3) are the diastereomeric esters of racemic menthol and l-amino acids.

The diastereomeric esters used in this invention are readily separable by chromatography on a broad diversity of chromatographic supports using a broad range of solvents as eluants. Column selectivity can be defined by the quantity, $$\alpha = \frac{(t_2 - t)}{(t_1 - t)} = \frac{k_2}{k_1}$$

where $t_2$ and $t_1$ are the retention times of the two diastereomers and t is the retention time of unretained components. This column selectivity, alpha, is a measure of the ease of separation of components on a particular support and with a particular solvent as eluant. Increasing values of alpha represent increasing ease of separation. Values of alpha greater than about 1.3 imply that the separation is quite facile; values of alpha from about 1.1 to about 1.3 imply that the separation is feasible although not necessarily facile. It has been observed that the diastereomers of racemic menthol used in this invention may have alpha values even greater than about 1.5.

The diastereomers used in this invention are esters from racemic menthol and amino acids, especially alpha-amino acids. Among the amino acids of this invention are the naturally occurring amino acids, such as alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine. In particular, the naturally occurring amino acids, which have the L-configuration, are especially desired as those used in the diastereomers of this invention.

However desirable the natural amino acids may be, other amino acids also can be utilized advantageously in the practice of this invention. Among these others are phenyglycine, nuclear substituted derivatives of phenylglycine such as 4-hydroxyphenylglycine, meta-tyrosine, 3,4-dihydroxyphenylalanine, and 3,5-diiodothyronine.

A solution of the diasteromeric esters is contacted with a chromatographic support. It has been found that a broad range of supports may be used in the practice of this invention. One group of preferred supports is represented by silica, alumina, and the zeolites. Another group of supports which may be used in the practice of this invention consists of supports commonly used for reverse phase chromatography. Reverse phase chromatography is that branch of chromatography where the mobile phase is more polar than the stationary phase, or support. Among the supports which are used in reverse phase chromatography are silicas modified by silanization so as to bear nonpolar groups on the surface of the silica as replacements for surface hydroxyl groups. For example, such silicas may bear long-chain alkyl, aryl, amino, or cyano groups bonded to the surface via a silicon-bearing moiety.

The chromatographic support is eluted with a solvent or solvent system under chromatographic conditions. By "chromatographic conditions" are meant those general principles of separation by chromatography known to those skilled in the art and routinely applied to a liquid-solid chromatographic operation. Thus, for example, solvent flow is uniform, formation of gas bubbles is avoided, disturbance of the solid support is minimized, and so forth. The solvents which may be used in the process of this invention are those typical of chromatographic processes. Among such solvents are aliphatic hydrocarbons such as pentane, hexane, heptane, octane, nonane, decane, cyclopentane, cyclohexane, diisobutylene, pentene, hexene, etc.; aromatic hydrocarbons such as benzene, toluene, the xylenes, ethylbenzene, diethylbenzene, methylethylbenzene and the like; halogenated hydrocarbons, especially chlorinated and fluorinated hydrocarbons illustrated by chloroform, methylene chloride, carbon tetrachloride, chloropropane, chlorobutane, chloropentane, fluoralkanes, bromoethane, chlorobenzene, chlorotoluene, and ethylene chloride; sulfides, especially carbon disulfide; ethers as illustrated by diethyl ether, tetrahydrofuran, tetrahydropyran, and dioxane; esters, especially acetates, such as methyl acetate, butyl acetate, and esters of saturated carboxylic acids up to about 6 carbon atoms where the portion arising from the alcohol is saturated and contains up to about 6 carbon atoms; ketones containing up to about 8 carbon atoms, such as acetone, butanone, pentanone, hexanone, heptanone, and octanone; nitroalkanes such as nitromethane, nitroethane, nitropropane, and nitrobutane; amines, especially pyridine; nitriles, such as acetonitrile, propionitrile, and butyronitrile; alcohols containing up to about 8 carbon atoms, including diols and triols; acetic acid and dimethylsulfoxide.

At least one effluent fraction is collected containing a purified diastereomer. Often the effluent is monitored for a particular property to determine suitable effluent fractions. For example, it may be monitored for a particular ultraviolet or infrared absorbance or for its refractive index, as representative of properties used to determine effluent fractions. Because the concentration of purified diastereomer may be low, differential measurements are especially valuable in determining effluent fractions.

After the effluent fraction or fractions containing a purified diastereomer is/are collected, the purified diastereomer is treated to liberate optically active menthol. Suitable methods of treating the purified diastereomer to afford optically active menthol include hydrolysis, alcoholysis, aminolysis, and reduction. Hydrolysis generally will be catalysed either by acid or base, with base catalysis being somewhat preferred to preserve the maximum optical purity of the liberated menthol as well as that of the liberated amino acid. Hydrolysis is a preferred treatment because the amino acid liberated concurrently can be readily recovered for reuse in a cyclic process. Mineral acids exemplify suitable acid catalysts; alkali metal hydroxide and carbonates exemplify suitable base catalysts.

Alcoholysis is the process whereby the menthyl portion of the diastereomeric ester is replaced by another alcohol, and represents transesterification where the alcohol portion of an ester is metathesized. Alcoholysis also is acid and base catalyzed, with base catalysis being preferred. Aminolysis is the process whereby the menthyl portion of the diastereomeric ester is replaced by an amine or ammonia. Such a process generally is self-catalyzed because of the nucleophilicity of the amine or ammonia used. Reduction represents another alternative to liberating optically active menthol from the purified diastereomer. In this treatment the carboxyl portion of the ester is reduced to a hydroxymethyl group to afford menthol and the alcohol derived from the amino acid portion of the ester. Reduction may be catalytic, using for example copper chromite as a catalyst, or it may be effected by chemical reducing agents such as lithium aluminum hydride, other aluminohydrides, lithium borohydride, and so on, to cite but a few examples.

It will be recognized by the skilled worker that there is a multitude of methods available in his arsenal for liberating optically active menthol from a purified diastereomer. It is to be emphasized that the particular method chosen is not critical; choices generally will be dictated by a desire to maximize chemical and optical yield while minimizing cost.

Regardless how the optically active menthol is liberated, it is then recovered by suitable means, as for example by crystallization.

The following examples merely illustrate this invention and are not intended to limit this invention in any way.

The chromatographic system employed in these examples was composed of a pump capable of flow rates up to 10 ml per minute at 10,000 psi, a septumless injector equipped with zero dead volume fittings, the appropriate column for separation, a dual-channel absorbance detector equipped for monitoring effluent at 254 and 280 nm, and a dual-channel recorder. All tubing used was stainless steel of 1/16" outside diameter with 0.009" inside diameter tubing. The columns were of stainless steel, 4.6 mm inside diameter and 25 cm long.

All solvents used as eluants were degassed and filtered before use. The hexane was freshly distilled and the forward phase eluants were dried using anhydrous magnesium sulfate. All eluants and other chemicals described were obtained from commercial sources and used without further purification.

EXAMPLE 1

To a single neck 200 ml round bottom flask equipped with a Dean-Stark trap and reflux condenser, a magnetic stirrer and a heating mantle was added 5.0 g (0.0331 moles) of D-(−)-phenylglycine, (l-phenylglycine), 6.0 g (0.0384 mole) of d,l-menthol, 7.30 g (0.0384 mole) of para-toluenesulfonic acid monohydrate, 5.3 ml benzene and 22 ml toluene. The slurry was heated at a gentle reflux with stirring for 5 days while water was removed by azeotropic distillation. The cooled slurry was filtered, the solid was treated with 10% aqueous sodium carbonate, and the resulting base mixture extracted with diethylether. The ether phase was dried (magnesium sulfate) and solvent was removed to afford 2.85 g of a crystalline mixture of the diastereomers plus unreacted menthol which was subsequently removed by sublimation. One of the diastereomers was separately prepared from l-menthol and l-phenylglycine in a like manner.

EXAMPLE 2

Separation of the diastereomers of racemic menthol prepared as described in Example 1 was achieved on a silica gel column using a 2-propanol-hexane solvent system as eluant. The insensivity of the separation to eluant composition is shown in the following table which gives the alpha values measured for various eluants.

| Alpha Values for 2-Propanol-Hexane Mixtures on Silica Gel | |
|---|---|
| Eluant, % 2-propanol | α |
| 20 | 1.53 |
| 10 | 1.54 |
| 5 | 1.51 |
| 1 | 1.44 |

The same diastereomer on a C-18 modified silica gel showed = 1.08 using as eluant 90% acetonitrile—10% 0.1 molar aqueous ammonium acetate.

EXAMPLE 3

Diastereomeric esters of menthol with different amino acids were prepared by the general method of Example 1 from l-menthol and racemic amino acids. Separation of each of the diastereomers was achieved on a silica gel column using 20% 2-propanol-hexane as the eluant. The accompanying table shows that the class of diastereomeric esters of menthol and an amino acid has alpha values leading to feasible chromatographic separation, with many members having an α-value making such separation quite facile.

| Alpha Values of Diastereomeric Esters of l-Menthol on Silica Gel Using 20% 2-Propanol-Hexane as Eluant | |
|---|---|
| Amino acid | α |
| phenylglycine | 1.53 |
| 4-hydroxyphenylglycine | 1.39 |
| tyrosine | 1.10 |
| phenylalanine | 1.14 |
| tryptophan | 1.30 |

EXAMPLE 4

A solution containing 2.44 g of a diastereomeric mixture prepared according to Example 1 was chromatographed on ca. 375 g silica gel using 5% 2-propanol-hexane as the eluant at a flow rate of 250 ml per minute using a commercial preparative chromatograph. The diastereomers were recycled twice and three fractions were collected. One fraction, 0.80 g, contained the l-d diastereomer in 99.9% purity. Another fraction amounting to 1.46 g contained the l-l diastereomer at 99.4% purity. The third fraction contained 0.16 g of the l-l diastereomer in 94.6% purity. Thus, the total recovery of diastereomers was over 99%.

EXAMPLE 5

To 1.04 g (0.00359 moles) of l-phenylglycine-l-menthylester in a 100 ml round bottom flask equipped with a magnetic stirrer was added 3 equivalents of sodium hydroxide dissolved in 10 ml of methanol. After 5 hours at room temperature, 20 ml of water was added to the reaction mixture and the resulting solution was extracted twice with about 20 ml portions of diethylether. The ether extracts were dried and concentrated to yield 0.41 g of l-menthol, $[\alpha]_D 18.6 = -48.1 \pm 1.2°$ (c 2.60, ethanol).

What is claimed is:

1. A method of preparing optically active menthol comprising contacting a solution containing the diastereomeric esters from racemic menthol and an optically active amino acid selected from the group consisting of naturally occurring amino acids, phenylglycine, 4-hydroxyphenylglycine, meta-tyrosine, 3,4-dihydroxyalanine, and 3,5-diiodothyronine with a chromatographic support, eluting said support with a solvent under chromatographic conditions, collecting at least one effluent fraction containing a purified diastereomer, treating the purified diastereomer to liberate optically active menthol, and recovering said optically active menthol.

2. The method of claim 1 where the naturally occurring amino acid is selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine.

3. The method of claim 2 where the amino acids have the L configuration.

4. The method of claim 1 where the chromatographic support is selected from the group consisting of silica, alumina, modified silicas and the zeolites.

5. The method of claim 1 where the optically active menthol is l-menthol.

6. The method of claim 7 where said hydrolysis is base catalyzed.

7. The method of claim 1 where the optically active menthol is liberated by hydrolysis.

8. The method of claim 1 where the optically active menthol is liberated by alcoholysis.

9. The method of claim 1 where the optically active menthol is liberated by aminolysis.

10. The method of claim 1 where the optically active menthol is liberated by reduction.

11. A method of obtaining a purified diastereomer from which l-menthol may be readily regenerated comprising contacting a solution containing the diastereomeric esters from racemic menthol and an optically active amino acid selected from the group consisting of naturally occurring amino acids, phenylglycine, 4-hydroxyphenylglycine, meta-tyrosine, 3,4-dihydroxyalanine, and 3,5-diiodothyronine, with a chromatographic support, eluting said support with a solvent under chromatographic conditions, and collecting at least one effluent fraction containing a purified diastereomer of l-menthol and said amino acid.

12. The method of claim 1 where the naturally occurring amino acid is selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine.

13. The method of claim 12 where the amino acids have the L configuration.

14. The method of claim 1 where the chromatographic support is selected from the group consisting of silica, alumina, modified silicas and the zeolites.

* * * * *